United States Patent
Lindsay

(10) Patent No.: US 7,556,633 B2
(45) Date of Patent: Jul. 7, 2009

(54) METHOD AND APPARATUS FOR ENDOSCOPIC DISSECTION OF BLOOD VESSELS

(75) Inventor: Erin Jessica Lindsay, Ann Arbor, MI (US)

(73) Assignees: Terumo Corporation, Shibuya-ku, Tokyo (JP); Olympus Medical Systems Corp., Shibuya-ku, Tokyo (JP)

( * ) Notice: Subject to any disclaimer, the term of this patent is extended or adjusted under 35 U.S.C. 154(b) by 1176 days.

(21) Appl. No.: 10/788,484

(22) Filed: Mar. 1, 2004

(65) Prior Publication Data

US 2005/0192613 A1    Sep. 1, 2005

(51) Int. Cl.
  *A61M 29/00* (2006.01)
  *A61B 17/32* (2006.01)
(52) U.S. Cl. .................... 606/159; 606/190; 606/170
(58) Field of Classification Search ............ 606/159, 606/170, 171, 180, 190, 41, 45, 48, 50; 600/114, 600/201, 210
See application file for complete search history.

(56) References Cited

U.S. PATENT DOCUMENTS

| | | | |
|---|---|---|---|
| 5,207,691 A | 5/1993 | Nardella |
| 5,527,319 A | 6/1996 | Green et al. |
| 5,569,291 A | 10/1996 | Privitera et al. |
| 5,655,545 A | 8/1997 | Johnson et al. |
| 5,695,514 A | 12/1997 | Chin |
| 5,792,135 A | 8/1998 | Madhani et al. |
| 5,855,583 A | 1/1999 | Wang et al. |
| 5,873,889 A | 2/1999 | Chin |
| 5,908,420 A | 6/1999 | Parins et al. |
| 5,913,866 A | 6/1999 | Ginn et al. |
| 5,916,233 A | 6/1999 | Chin |
| 5,980,549 A | 11/1999 | Chin |
| 6,004,335 A | 12/1999 | Vaitekunas et al. |
| 6,019,771 A | 2/2000 | Bennett et al. |

(Continued)

FOREIGN PATENT DOCUMENTS

WO    WO 03/000139 A1    1/2003

OTHER PUBLICATIONS

Schultz, Leonard S. et al., "Using 5-mm Bipolar Cutting Forceps: A New Multifunctional Instrument," Journal of Laparoendoscopic & Advanced Surgical Techniques, vol. 7, No. 6, Dec. 1977, Mary Ann Liebert, Inc., Larchmont, New York, pp. 375-378.

(Continued)

*Primary Examiner*—Vy Q Bui
(74) *Attorney, Agent, or Firm*—Buchanan Ingersoll & Rooney PC

(57) ABSTRACT

An endoscopic apparatus for dissecting a blood vessel includes a endoscopic barrel having a plurality of lumens, one of the lumens being dimensioned for receiving an endoscope, a handle disposed at a proximal end of the endoscopic barrel, at least two fingers having distally curved ends for dissecting and cauterizing the desired blood vessel, and a displaceable cone portion disposed over a distal end of the endoscopic barrel. The cone portion has a first position concealing the at least two fingers and a second, extended position exposing the at least two fingers. A control rod extends between the handle and each of the fingers such that movement of the control mechanism between a first position and a second position produces a predetermined movement of the respective finger.

17 Claims, 5 Drawing Sheets

U.S. PATENT DOCUMENTS

| | | | |
|---|---|---|---|
| 6,022,313 A | 2/2000 | Ginn et al. | |
| 6,030,406 A | 2/2000 | Davis et al. | |
| 6,132,441 A | 10/2000 | Grace | |
| 6,143,008 A * | 11/2000 | Eaves, III | 606/159 |
| 6,179,854 B1 | 1/2001 | Nash et al. | |
| 6,193,653 B1 | 2/2001 | Evans et al. | |
| 6,203,559 B1 | 3/2001 | Davis et al. | |
| 6,206,823 B1 | 3/2001 | Kolata et al. | |
| 6,206,877 B1 | 3/2001 | Kese et al. | |
| 6,206,903 B1 | 3/2001 | Ramans | |
| 6,264,670 B1 | 7/2001 | Chin | |
| 6,309,397 B1 | 10/2001 | Julian et al. | |
| 6,312,435 B1 | 11/2001 | Wallace et al. | |
| 6,352,544 B1 | 3/2002 | Spitz | |
| 6,375,635 B1 | 4/2002 | Moutafis et al. | |
| 6,527,771 B1 | 3/2003 | Weadock et al. | |
| 6,660,016 B2 | 12/2003 | Lindsay | |
| 2003/0212420 A1 | 11/2003 | Gruhl et al. | |
| 2004/0133228 A1* | 7/2004 | Bayer | 606/190 |

OTHER PUBLICATIONS

Gossot, D. et al., "Ultrasonic Dissection for Endoscopic Surgery," Surgical Endoscopy, (1999) 13: 412-417.

Dziedzic, Ryan P. et al., "Design of Multifunctional Compliant Mechanisms for Minimally Invasive Surgery," Proceedings of DETEC'01—ASME 2001 Design Engineering Technical Conference, Pittsburgh, PA, Sep. 9-12, 2001, pp. 441-450.

"Endoscopic Vessel Harvesting," http:www.guidant/com/products/endoscopic.shtml, Jul. 26, 2005, p. 1 of 1.

European Search Report ((EP 05 00 4460) mailed Jul. 12, 2005.

* cited by examiner

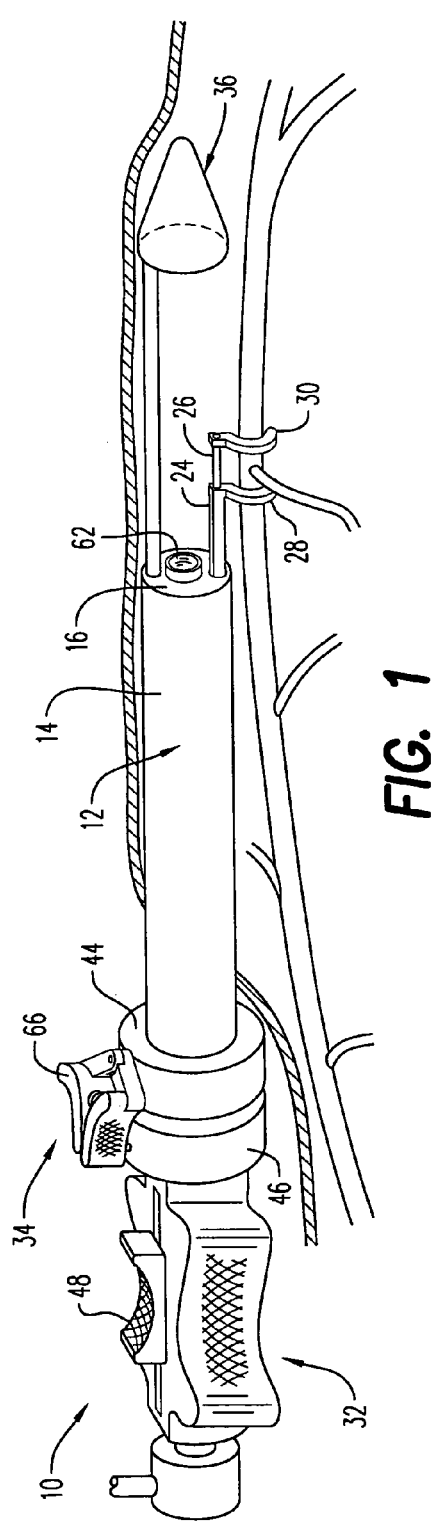
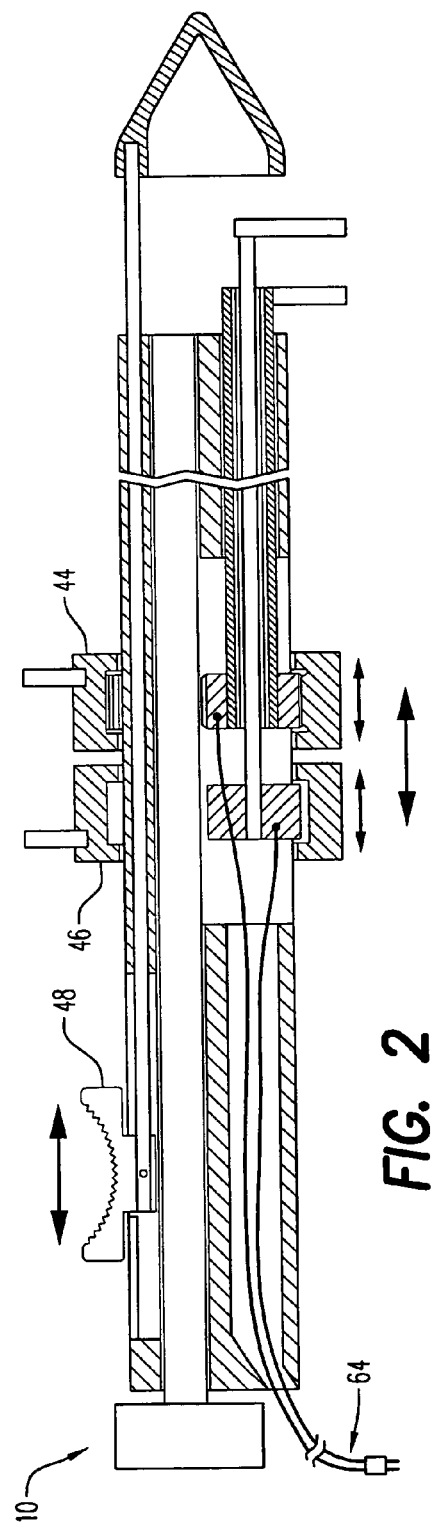

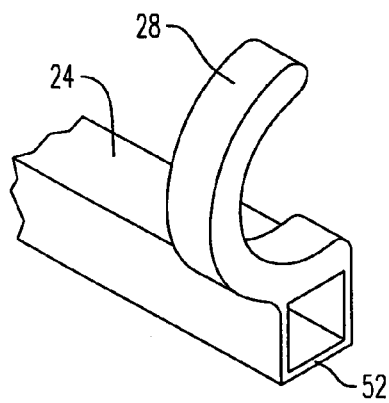 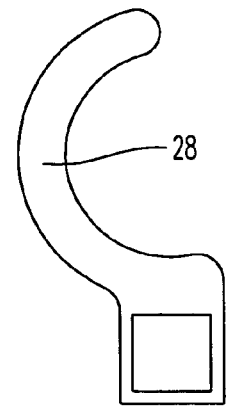
FIG. 8A    FIG. 8B
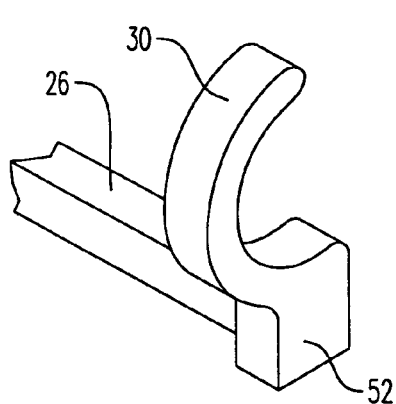 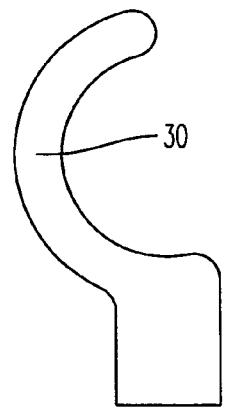
FIG. 9A    FIG. 9B

METHOD AND APPARATUS FOR ENDOSCOPIC DISSECTION OF BLOOD VESSELS

BACKGROUND OF THE INVENTION

The present invention relates to the harvesting of blood vessels and, more particularly, to methods and apparatus for endoscopic dissection of sections of blood vessels, such as saphenous veins, for use as a coronary artery bypass graft.

It is common during various surgical procedures, and most particularly during coronary artery bypass grafting (CABG), to remove or "harvest" 0 a blood vessel or vessel section, such as an artery or vein, from its natural location in a patient's body and to use it elsewhere in the body. In CABG surgery, the blood vessel is used to form a bypass between an arterial blood source and the coronary artery that is to be bypassed. Often an artery proximate the heart, such as one of the internal mammary arteries, can be used as the bypass graft, although the saphenous veins in the legs, or a radial artery in an arm can also be used as well.

The conventional surgical procedure used to harvest a section of the saphenous vein, or the like, for use in the CABG surgery involves making a continuous incision in the leg for the full length of the desired vein section in order to provide adequate exposure for visualizing the vein and for introducing surgical instruments to sever, cauterize and ligate the tissue and side branches of the vein. The incision must then be closed by suturing or stapling along its length.

Less-invasive techniques for harvesting blood vessels have also been developed which employ only two small incisions, generally one at each end of the section of vessel to be removed. Primary dissection occurs by introduction of one or more surgical instruments through a first incision to create a working space and separate the vein from the surrounding tissue. Then further instruments are introduced into the generally limited working space to dissect the blood vessel from the connective tissue surrounding the section to be harvested. The side branches of the blood vessel are also clipped and/or cauterized. In order to remove the desired section of the blood vessel, a second small incision, or stab wound, is made at the distal end thereof and the distal end of the blood vessel section is ligated. The proximal end of the blood vessel section is then also ligated, thereby allowing the desired section to be completely removed through the first incision. An endoscopic instrument is generally required for such a procedure to enhance visualization of the vessel and the surrounding tissue and to properly position the surgical instrument. Example of such endoscopic instruments for harvesting blood vessels are shown in U.S. Pat. No. 6,193,653 to Evans et al. and U.S. Pat. No. 6,019,771 to Bennett et al.

These types of less invasive techniques reduce the overall length of the incision, as well as the trauma to the blood vessel section and the surrounding tissue. The introduction of a plurality of surgical instruments through the incision, however, may still cause some irritation or damage to the vessel which must then be repaired before it can be used as a graft.

Accordingly, it would be desirable to have a vessel harvesting device and procedure that minimizes the number of surgical instruments that must be inserted into the patient's body and that provides for more precise manipulation of the blood vessel by a surgeon.

SUMMARY OF THE INVENTION

The present invention provides an endoscopic apparatus for harvesting blood vessels which has an endoscopic barrel including a plurality of lumens, one of the lumens being dimensioned for receiving an endoscope. A handle is disposed at a proximal end of the endoscopic barrel and a cone portion is extendable from a distal end of the endoscopic barrel to expose two finger elements for dissecting and cauterizing a blood vessel.

In a preferred embodiment, the two fingers preferably have distally curved ends defining hooks with a radius of curvature compatible with the endoscopic barrel. More particularly, one of the fingers defines an inner finger and the other finger defines an outer finger such that, when the fingers are axially aligned, the inner and outer fingers form a shear plane therebetween for severing and cauterizing tissue, such as a blood vessel.

The rotational movement of the fingers is controlled such that the inner and outer fingers rotate together. The longitudinal movement of the fingers is controlled by a control mechanism within the handle such that the fingers can be extended and retracted independently or together, and one of the fingers is also independently controlled such that it can close a space defined between the fingers, thereby pinching and severing the tissue therebetween. The control mechanism includes, amongst other components, a control rod extending from the handle to each respective finger such that movement of the control mechanism between a first position and a second position produces a predetermined longitudinal movement of the respective finger.

DETAILED DESCRIPTION OF THE FIGURES

These, and other objects, features, and advantages of the present invention will become more readily apparent to those skilled in the art upon reading the following detailed description, in conjunction with the appended drawings in which:

FIG. 1 is a perspective view of an endoscopic vein dissector and cauterizing apparatus with the cone portion and the fingers extended for dissecting a blood vessel according to a preferred embodiment of the present invention.

FIG. 2 is a cross-sectional view thereof.

FIG. 8A is a perspective view of the inner finger of FIG. 4 and FIG. 8B is an end view thereof.

FIG. 9A is a perspective view the outer finger of FIG. 4 and FIG. 9B is an end view thereof.

DETAILED DESCRIPTION OF THE PREFERRED EMBODIMENT OF THE INVENTION

Figure 3:
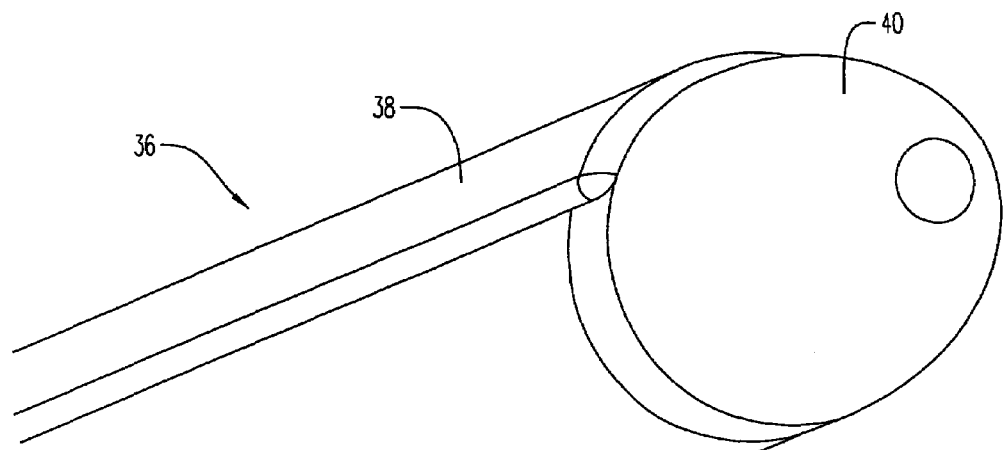
FIG. 3 is an enlarged perspective view of the vein dissector of the apparatus shown in FIG. 1, when the cone portion is in a closed position for primary dissection.

An endoscopic vein dissector and cauterizing apparatus according to the present invention is shown generally by reference numeral 10 in FIGS. 1 and 2. The vein dissector and cauterizing apparatus 10 comprises an endoscopic tube 12, a handle 32 having a push tab 48 and control mechanism 34, an extendable cone portion 36, and rotatable and extendable inner and outer fingers 28, 30, for dissecting, severing and cauterizing a desired blood vessel. The endoscopic apparatus 10 is utilized with the cone portion 36 in a closed, or retracted position, as shown in FIG. 3, when performing the primary dissection of the tissue from around a section of the desired blood vessel which is to be harvested, and thus creates a working space surrounding the selected section. The cone portion 36 includes an arcuate sheath portion 38 and a cone tip 40. The cone tip 40 is preferably formed from a transparent material, such as polycarbonate or other suitable material, so as to enable the surgeon to visualize the position of the integrated apparatus 10 through the lens of the endoscope.

The endoscopic tube 12 preferably includes a flexible outer sheath 14, and a coaxial inner member 16 which forms at least two passages or lumens 18, 20 extending the length thereof. Lumen 18 is generally the largest of the two lumens so as to accommodate the insertion of a conventional imaging system, or endoscope, having an optical lens arrangement 62 (FIG. 4) connected to an optical fiber and camera. Preferably, a zero degree endoscope is utilized, thereby allowing the surgeon to visualize the blood vessel directly in front of the apparatus 10, as discussed further below, but other endoscopes could of course also be used. The lumen 20 preferably accommodates control rods 24, 26, respectively, for movement of the inner and outer fingers 28, 30, as shown in FIGS. 4-7 and discussed further below. Preferably, the inner member 16 is rotatable about the imaging system or endoscope within the lumen 18. That is, the inner member 16, along with the cone portion 36 and the fingers 28, 30 may be rotated about a fixed lens 62. This is useful in maintaining a frame of reference for the surgeon because the field of vision will not be rotating during the operation.

Figure 4:
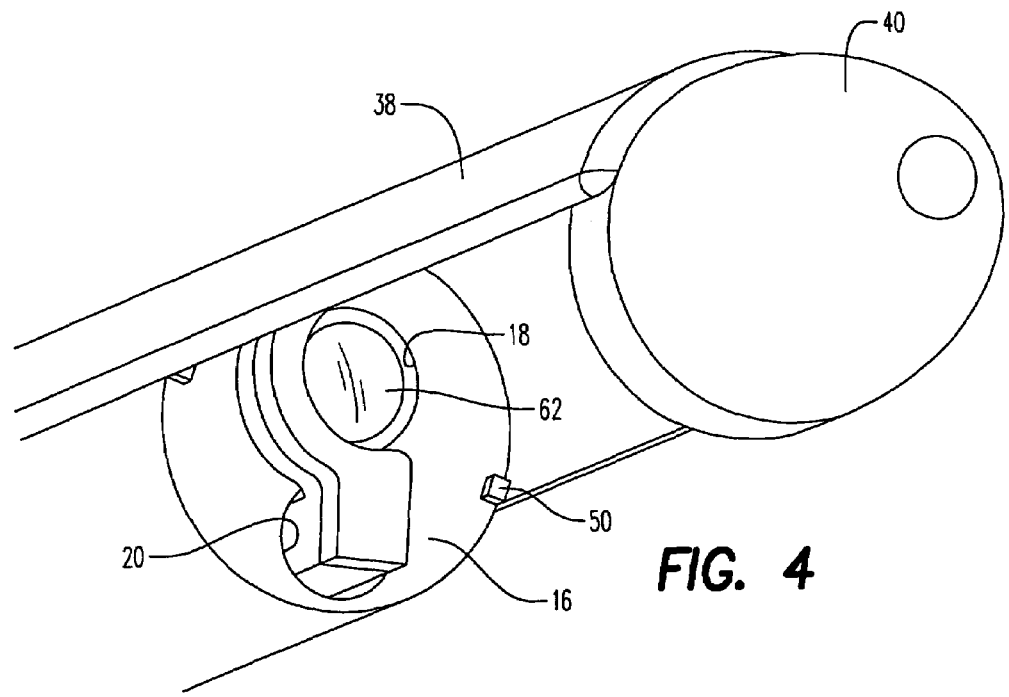
FIG. 4 is an enlarged perspective view thereof when the cone is in an extended position and the fingers are disposed in a storage position.

After performing the primary dissection and without removing the apparatus 10 from the first incision, the cone portion 36 may be extended away from the distal end portion 42 through movement of the push tab 48. The sheath 38 is preferably secured about the tube 12 on a track system 50 extending the length thereof. Accordingly, forward movement of the push tab 48 correspondingly moves the sheath 38 and cone tip 40 in a forward, or distal, direction, thereby exposing the inner and outer fingers 28, 30, as shown in FIG. 4. The handle 32 preferably includes a recessed area on one surface thereof. The recessed area thus defines a front stop and a rear stop which limits the movement of the push tab 48. The tab 48 may be mounted to a depending slider element which extends downward through a top plate. Thus, the push tab 48 is preferably slidable along the top plate within the recessed area, as defined between the front stop and the rear stop.

Although the use of two fingers, as described below is a preferred embodiment of the present invention for dissecting, severing and cauterizing a blood vessel, one skilled in the art will recognize that other possible means may utilize only one or more than two dissecting and cauterizing elements. Each of the fingers 28, 30 is preferably a bipolar electrode, although a monopolar electrode could of course also be used. More preferably, each finger includes a bipolar insulator and an electrical conductor. As illustrated, each of the fingers 28, 30 may have a generally curved configuration generally resembling a hook portion on the terminal end thereof. The hook-shaped configuration, in combination with the rotational and longitudinal movement of the fingers 28, 30, enable the fingers to be used in removing connective tissue from the blood vessel. The hook-shaped configuration is also preferred to allow the fingers to be compactly arranged about the endoscope lens 62, as shown in FIG. 4. In this regard, the size and radius of curvature of the hook-shaped fingers preferably corresponds or is compatible with that of the lumen 18.

Figure 5:
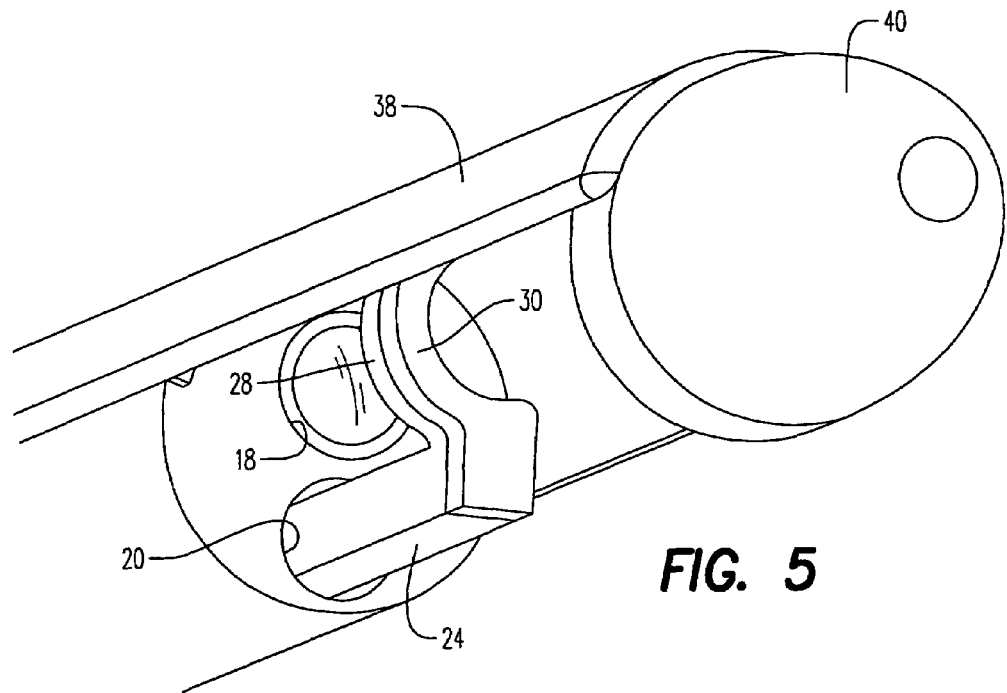
FIG. 5 illustrates the fingers shown in FIG. 4 in an extended position.

Referring also to FIG. 5, the movement of the fingers 28, 30 is preferably controlled by a control mechanism 34 disposed on the handle 32 of the apparatus 10. The control mechanism 34 preferably includes finger pinch tabs 66 and finger controls rings 44, 46, control ring 44 controlling the movement of inner finger 28 while control ring 46 controls outer finger 30 movement. The control rings 44, 46 are connected to the fingers 28, 30, respectively, by control rods 24, 26 which extend through lumen 20 within the endoscopic tube 12. As shown most clearly in FIG. 6, the control rod 24 is preferably hollow and receives control rod 26 therein such that both control rods are within a single lumen 20. It is also within the scope of the present invention, however, to provide separate lumens for each of the control rods. The distal end of each control rod 24, 26 connects to the attachment base 52 of the finger and thereby translates the motion of the control into the appropriate finger movement. The finger control rings 44, 46 may be moved in a sliding direction along a line parallel to the longitudinal axis of the endoscopic tube 12. The control rings 44, 46 preferably move together for a predetermined distance, thereby extending the fingers 28, 30 outwardly a sufficient distance from the endoscopic lens. Thereafter, one control ring may be further moved in a forward or rearward direction to create a predefined distance between the fingers 28, 30 into which a blood vessel may be received. As shown best in FIG. 7, the fingers 28, 30 are also capable of movement together within an approximately 180° clockwise or counter-clockwise range by rotation of control rings 44 and 46. With reference to FIGS. 8A, 8B, 9A and 9B, in the preferred embodiment, the configuration of the control rods 24, 26 restricts the fingers 28 and 30 to simultaneous rotation.

Figure 6:
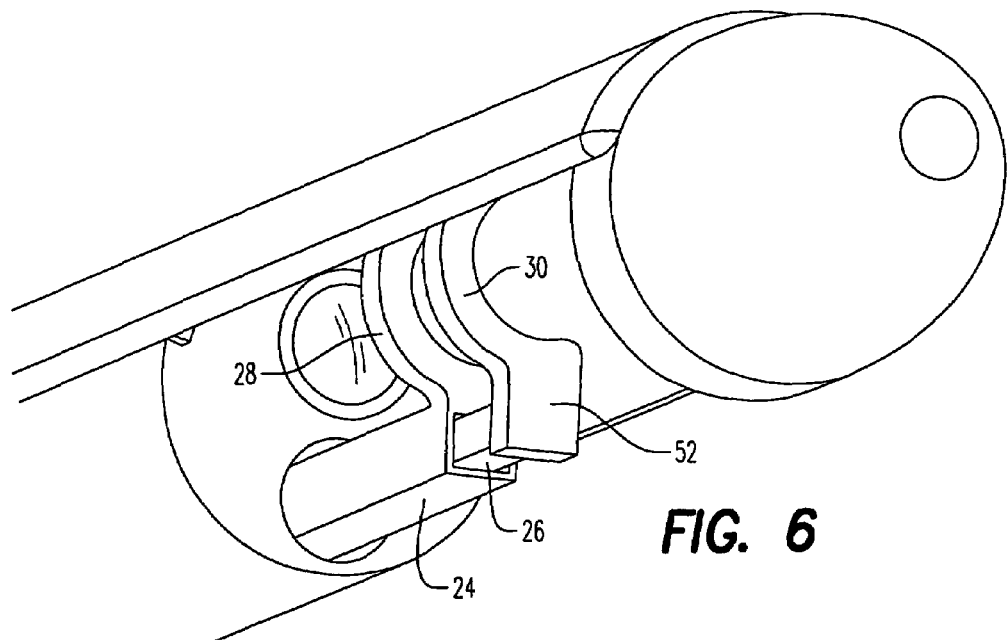
FIG. 6 illustrates the fingers shown in FIG. 5 when the outer finger is further extended independently of the inner finger.
Figure 7:
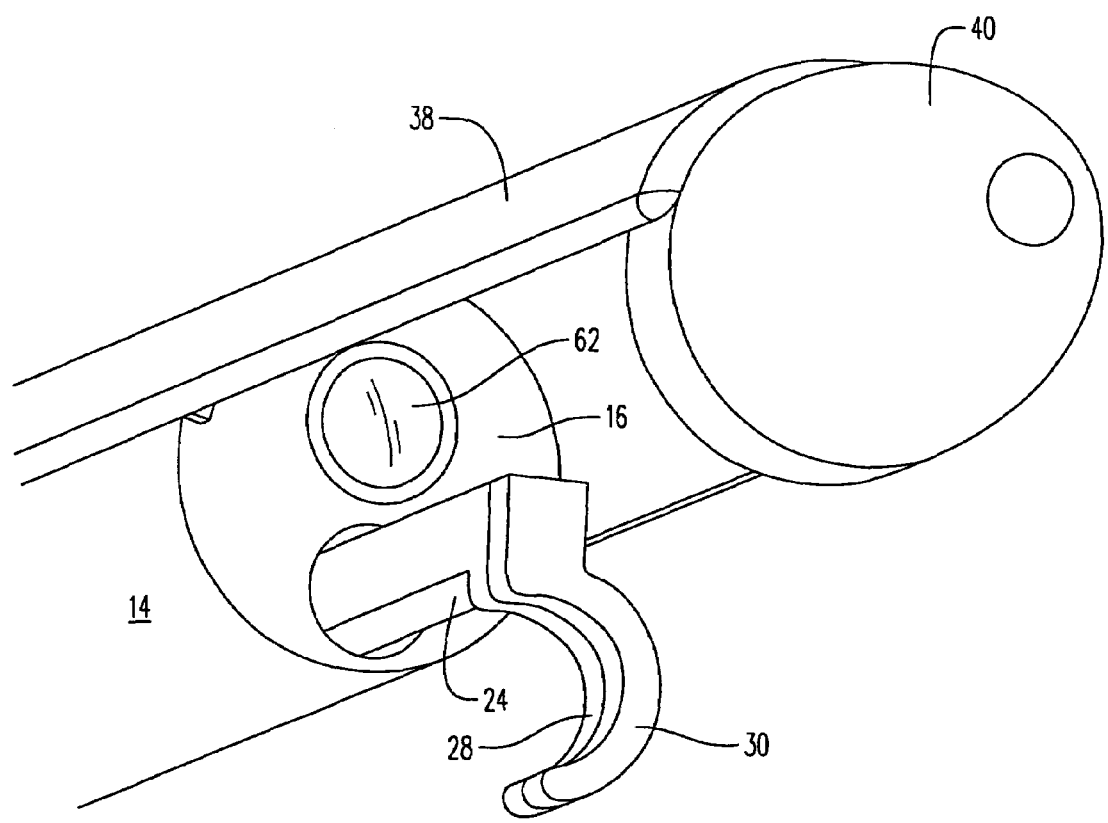
FIG. 7 illustrates the fingers shown in FIG. 5 in a rotated position.

By manipulation of the control rings 44, 46, a user can control the movement and position of each of the fingers 28, 30, thus allowing the fingers to be rotated, extended and/or retracted to form a spaced opening therebetween for tissue dissection, as shown in FIG. 6, or to be aligned one in front of the other for pinching when the fingers are to be used for severing and cauterizing, as shown in FIG. 5. More particularly, the control rings 44, 46 are manipulated to properly position the fingers 28, 30 around a blood vessel, and the finger pinch tabs 66 are then squeezed together—causing the fingers to come together and "pinch" the blood vessel. As mentioned above, disposed in each of the fingers 28, 30 is a cauterizing bipolar insulator. Each bipolar insulator is electrically conducted and connected via a power cord 64 to a source of electric energy for cauterizing a severed end of a blood vessel. Thus, because the fingers are also electrodes, the tissue between the fingers completes an electrical circuit and thus energizes the electrodes to thereby cauterize the tissue as it is being severed. The electrodes are preferably energized by a foot operable pedal, so as not to require use of the surgeon's hands.

The above description of the relative movement between the control rings, the finger pinch tabs, and the respective fingers is preferred for the illustrated embodiment; however, other arrangements would of course also be possible.

In operation a section of a desired blood vessel, such as the saphenous vein, may be harvested using the integrated apparatus 10 of the present invention in the following manner. A small incision is formed at an appropriate location in a patient's leg adjacent the saphenous vein. With the cone portion 36 in position on the endoscopic tube 12, a distal end of the apparatus 10 may be inserted through the incision and advanced forward to perform the primary dissection, so as to separate the tissue from the vein and create a working space thereround. As known in the art, gas insufflation, such as with carbon dioxide, may be used to maintain the working space in its expanded form.

After the primary dissection, the apparatus 10 preferably remains in place and the cone portion 36 is moved distally so as to expose the fingers 28, 30. Thus, the present invention eliminates the necessity of removing and then reinserting an apparatus through the incision in order to proceed with the branch dissection. The inner fingers 28 and 30 are preferably extended distally away from the lens 62 and may be separated, for example, with the outer finger disposed further distally than the inner finger so as to enable the vein to be disposed therebetween. Because the endoscope is preferably positioned above and to the rear of the fingers 28, 30, the optical lens 62 of the endoscope can clearly view the fingers 28, 30 and the tissue to be dissected; thereby providing optimal observation for guiding and operating the apparatus 10. In this manner the fingers 28, 30 can dissect the vein from the connective tissue and cut any side branches along the vein simply by movement of the fingers to the axially adjacent position shown in FIG. 6. After removing the side branches and connective tissue, a second small incision or stab wound may be made at the distal end. It is preferable, however, if a second incision is to be made, to do so when the cone portion is disposed on the endoscopic tube, such that the second stab wound may contact the cone portion 36 rather than risk damage to the desired blood vessel section. After ligation and cutting of the distal end of the desired blood vessel section, the proximal end of the section may then also be ligated and cut, thereby allowing the desired section of the vein to be pulled through the first small incision.

The pinch tabs 66 and control rings 44, 46 of the present invention allow the apparatus 10 to be used with only one hand of the surgeon, thereby freeing a second hand, for example, to hold and reposition the patient's leg, which is frequently necessary in order to obtain the best angle for harvesting of the saphenous vein. Further, while slidable and rotatable control rings are shown as the preferred mechanism for obtaining the desired movement of the fingers, it should be apparent to one skilled in the art that other control mechanisms can of course also be used. Possible variations would include a thumb control for rotating pulleys to move cables and thereby operate the fingers. Further possible control mechanisms would include independent rack and pinion mechanisms which are again preferably controlled by the thumb of the user so as to enable single hand operation.

The present invention has now been described with reference to a preferred embodiment thereof. The foregoing detailed description has been given for clarity and understanding only. No unnecessary limitations are to be understood therefrom. It will be apparent to those skilled in the art that many changes can be made in the embodiment described without departing from the scope of the invention. Thus, the scope of the present invention should not be limited to the exact details and structures described herein, but rather by the structures described by the language of the claims, and the equivalents of those structures.

What is claimed is:

1. An endoscopic apparatus for dissecting a desired blood vessel comprising:
   an endoscopic barrel including at least two lumens, one of said lumens dimensioned for receiving an endoscope;
   a handle disposed at a proximal end of the endoscopic barrel;
   at least two fingers disposed within the endoscopic barrel for dissecting and cauterizing the desired blood vessel, said fingers having a hook-shaped configuration; and
   a displaceable cone portion disposed over a distal end of said endoscopic barrel;
   wherein the cone portion has a first position concealing the at least two fingers and a second, extended position exposing the at least two fingers, and
   wherein said at least two fingers are rotatable relative to longitudinal axis of one or said lumen and each of said at least two fingers is independently extendable in an axial direction so as to define a space between said at least two fingers for receiving the desired blood vessel.

2. The apparatus of claim 1, further comprising an endoscope extending through one of said lumens.

3. The apparatus of claim 1, wherein each of said at least two fingers includes a bipolar electrode for severing and cauterizing tissue between said two fingers when an electrical circuit is completed for cauterizing tissue therebetween.

4. The apparatus of claim 1, wherein when said at least two fingers are rotated about the longitudinal axis, said fingers are disposed beyond the periphery of said endoscopic barrel.

5. The apparatus of claim 1, wherein said displaceable cone portion includes a longitudinal portion and a cone tip portion.

6. The apparatus of claim 5, wherein said cone tip portion is substantially transparent.

7. The apparatus of claim 6, wherein said handle further includes a control tab for controlling longitudinal movement of said displaceable cone portion.

8. The apparatus of claim 7, wherein said control tab is mounted within a recessed area, the recessed area defining a front stop and a rear stop which limits the movement of said control tab.

9. The apparatus of claim 1, wherein said hooked-shaped fingers include distal curved ends, a size and radius of curvature of the curved ends being compatible with one of said lumens such that said fingers may be compactly arranged about the endoscope.

10. The apparatus of claim 9, wherein one of said fingers defines an inner finger and another of said fingers defines an outer finger such that, when said fingers are axially adjacent one another, said inner and outer fingers form a plane therebetween for severing tissue.

11. The apparatus of claim 9, wherein said handle includes a control mechanism for controlling each of said fingers.

12. The apparatus of claim 11, wherein said control mechanism comprises a movable control ring for each said finger disposed on said handle, said movable control ring controlling rotational and longitudinal movement of said respective finger.

13. The apparatus of claim 12, wherein each said control ring is connected to a control rod, a distal end of the control rod being connected to one of said fingers such that movement of said control ring between a first position and a second position produces predetermined movement of said one of said fingers.

14. The apparatus of claim 13, wherein said control rings move together in rotational direction and together or independently in a longitudinal direction.

15. The apparatus of claim 13, wherein said endoscopic barrel includes two lumens, said control rods extending through one of said lumens.

16. The apparatus of claim 12, wherein said control mechanism further comprises a pair of pinch tabs.

17. The apparatus of claim 16, wherein movement of said pinch tabs towards one another causes said fingers to move axially adjacent one another, said inner and outer fingers forming a plane therebetween for severing tissue.

* * * * *